US00PP19464P2

(12) United States Plant Patent
Korlipara

(10) Patent No.: US PP19,464 P2
(45) Date of Patent: Nov. 18, 2008

(54) ***ECHINACEA* PLANT NAMED 'MAC 'N' CHEESE'**

(50) Latin Name: ***Echinacea* spp.**
Varietal Denomination: Mac 'n' Cheese

(76) Inventor: Harini Korlipara, Canby, OR (US)

( * ) Notice: Subject to any disclaimer, the term of this patent is extended or adjusted under 35 U.S.C. 154(b) by 0 days.

(21) Appl. No.: 11/999,760

(22) Filed: Dec. 6, 2007

(51) Int. Cl.
*A01H 5/00* (2006.01)

(52) U.S. Cl. ..... Plt./428

(58) Field of Classification Search ..... Plt./428
See application file for complete search history.

*Primary Examiner*—Annette H Para

(57) ABSTRACT

A new and distinct *Echinacea* plant named 'Mac 'n' Cheese' characterized by large, bright orange-yellow flowers, ray florets held perpendicular to the stem, well-branched upright flower stalks, and excellent vigor.

1 Drawing Sheet

Botanical denomination: *Echinacea* spp.
Variety designation: 'Mac 'n' Cheese'.

The present invention relates to a new and distinct cultivar of *Echinacea* and given the cultivar name 'Mac 'n' Cheese'. *Echinacea* is in the family Asteraceae. This new cultivar originated as a fourth generation seedling from a planned breeding program using the parents *Echinacea paradoxa* (unpatented) and *Echinacea purpurea* 'Ruby Giant' (unpatented) for the initial cross. The exact parents of this selection are unnamed proprietary, unreleased plants.

This new *Echinacea* cultivar is distinguished by:

1. Large, bright orange-yellow flowers
2. Ray florets held perpendicular to the stem
3. Well-branched upright flower stalks
4. Excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
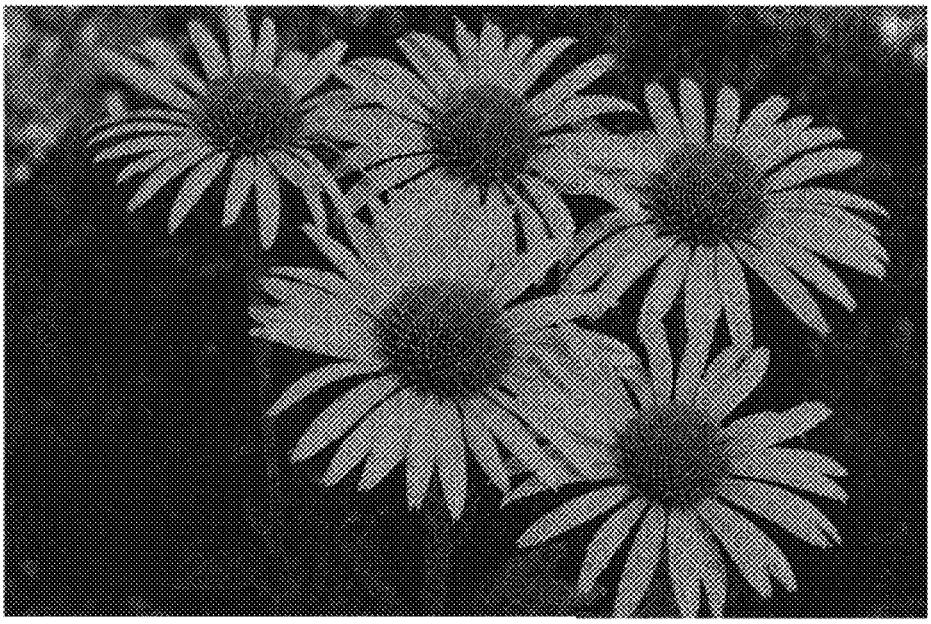
FIG. 1 shows the flowers of *Echinacea* 'Mac 'n' Cheese' cut from a plant growing in the ground in full sun in the field in late summer in Canby, Oreg.

The following is a detailed description of the new *Echinacea* cultivar based on observations of a 9-month-old specimen growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—40 cm wide and 70 cm tall to top of flowers.
- *Form.*—Basal clump.
- *Vigor.*—Excellent.
- *Roots.*—Fibrous, with many downward growing and few laterals, ivory in color (Yellow White 158D), roots develop easily from cuttings from the crown.

Stem (flowering):
- *Type.*—Ascending.
- *Size.*—Branching to 70 cm tall to a terminal flower and 1.3 cm wide at base.
- *Internode length.*—2 cm to 6.5 cm.
- *Surface texture.*—Strigose.
- *Color.*—Yellow Green 146C mottled with Yellow Green 146A.

Leaf (basal and stem):
- *Type.*—Simple.
- *Shape.*—Lanceolate to broadly lanceolate.
- *Arrangement.*—Basal, stem leaves alternate.
- *Blade size.*—Grows to 17 cm long and 5.5 cm wide.
- *Margins.*—Entire.
- *Apex.*—Acuminate.
- *Base.*—Attenuate, continuing down petiole, clasping.
- *Surface texture.*—Strigose on both sides.
- *Venation.*—Pinnate.
- *Color.*—Topside — Yellow Green 147A with the vein Yellow Green 147B; Bottom — Yellow Green 147A with the vein Yellow Green 147C.
- *Petiole description.*—Grows to 8 cm long and 3 mm wide, strigose, Yellow Green 147C.

Inflorescence:
- *Type.*—Composite on stalked terminal heads.
- *Number of flowering stems per plant in summer.*—2 to 5.
- *Flowering stem.*—Grows to 70 cm tall from the base of the plant to the terminal flower and can grow to 22 cm long from the top leaf to the base of a flower head; may branch 0 to 5 times; diameter growing to 11 mm wide near the flower head; strigose;

branched, with two to five branches, Yellow Green 145B mottled with Yellow Green 146B.

*Size.*—Grows to 11.5 cm wide and 4.5 cm deep as disc enlarges.

*Form.*—Ray petals cup downward slightly, mature disc is conic.

*Immature inflorescence.*—3 cm wide and 3 cm deep, ray petals held upright and colored Greyed Yellow 162B with tips Yellow Green 153B, disc is Yellow Green 146A.

*Ray florets.*—Without pistil or stamen, 31 to 36 in number, each oblanceolate to lanceolate with the tip two to three toothed, entire margins, base attenuate, sometimes overlapping, grows to 5 cm long and 7 mm wide, glabrous on both sides; topside color of young ray florets Yellow Orange 23A lightening to 21B and finally fading to Yellow 11C, bottom side color Yellow Orange 20D lightening to Yellow Orange 16C and finally to Yellow 11D.

*Disc.*—Flat becoming conic, 3.3 mm to 5.3 mm wide and becoming 3 cm deep with maturity, overall color two toned with Yellow Green 144A in the background with Yellow Orange 23A in the foreground.

*Disc florets.*—About 400 in number, each 11 mm long and 1.2 mm wide, each with one persistent, very stiff bract (8 to 9 mm long and Yellow Orange 23A on top half, Yellow Green 144A on bottom half); corolla 6 mm long and 1.5 mm wide, 5 lobed, glabrous, Yellow Green 144D; overlay White 155D, 4 mm long; pistil 6 mm long and 1.5 mm wide, with an extruding, 2-branched stigma, spreading 3.5 mm wide, Yellow Green 150C, style 6 mm long, Yellow 13A on top half and Yellow Green 144D on bottom half; stamen 4 in number, Greyed Orange 164B, 5 mm long, anthers 3 mm long and Brown 200A, filaments 3 mm long, Yellow White 158C, pollen Yellow Orange 17C.

*Phyllaries.*—In 4 leafy series, area 4.5 cm wide and 12 mm deep, lobes lanceolate in shape, reflexed, grow to 13 mm long and 3 mm wide, Yellow Green 147B, margins strigose, tip acute.

*Receptacle.*—Grows to 20 mm wide and 25 mm deep, White 155D.

*Bloom period.*—July through October in Canby, Oreg.

*Fragrance.*—Lovely, floral.

*Bloom time.*—Summer until frost in Canby, Oreg.

*Lastingness.*—Each inflorescence lasts about two weeks in Canby, Oreg.

Seeds: Average number of 24 seeds/head, each 4 mm long and 2.5 mm wide, oval, Grey Brown 199C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea* 'Ruby Giant', an unpatented plant and the original seed parent in the breeding line, the new variety has orange-yellow rather than red-purple flowers.

Compared to *Echinacea paradoxa* (unpatented), the original pollen parent in the breeding line, the new variety is shorter, orange-yellow rather than yellow, more ray florets, and with ray florets held at right angles to the stem rather than strongly reflexed.

Compared to *Echinacea* 'Sunrise' (U.S. Plant Pat. No. 16,235), the new variety has larger flowers of a deeper yellow, that hold their color and don't fade.

Compared to *Echinacea* 'Matthew Saul' (U.S. Plant Pat. No. 17,652), the new variety has flowers that don't reflex, of a brighter yellow, that hold their color longer.

I claim:

1. A new and distinct *Echinacea* plant as herein illustrated and described.

* * * * *

UNITED STATES PATENT AND TRADEMARK OFFICE

CERTIFICATE OF CORRECTION

PATENT NO. : PP 19,464 P2
APPLICATION NO. : 11/999760
DATED : November 18, 2008
INVENTOR(S) : Harini Korlipara It is certified that error appears in the above-identified patent and that said Letters Patent is hereby corrected as shown below:

On the cover page of the patent, please enter the following:

(73) Assignee: Terra Nova Nurseries, Inc., Canby, Oregon 97103 (US)

(74) Attorney, Agent, or Firm - Klarquist Sparkman, LLP

Signed and Sealed this

Twenty-third Day of June, 2009

JOHN DOLL
*Acting Director of the United States Patent and Trademark Office*